(12) United States Patent
Anderson et al.

(10) Patent No.: US 10,124,147 B2
(45) Date of Patent: Nov. 13, 2018

(54) GUIDE EXTENSION CATHETERS AND METHODS FOR MANUFACTURING THE SAME

(71) Applicant: BOSTON SCIENTIFIC SCIMED, INC., Maple Grove, MN (US)

(72) Inventors: James M. Anderson, Fridley, MN (US); Joel M. Wasdyke, Eden Prairie, MN (US); Huisun Wang, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 490 days.

(21) Appl. No.: 13/953,534

(22) Filed: Jul. 29, 2013

(65) Prior Publication Data

US 2014/0039461 A1  Feb. 6, 2014

Related U.S. Application Data

(60) Provisional application No. 61/678,502, filed on Aug. 1, 2012.

(51) Int. Cl.
*A61M 25/00* (2006.01)
*A61B 17/34* (2006.01)
(Continued)

(52) U.S. Cl.
CPC ..... *A61M 25/0069* (2013.01); *A61B 17/3415* (2013.01); *A61M 25/001* (2013.01);
(Continued)

(58) Field of Classification Search
CPC ........ A61M 2025/0004; A61M 25/005; A61M 2025/1081; A61M 2039/062;
(Continued)

(56) References Cited

U.S. PATENT DOCUMENTS 4,564,014 A   1/1986  Fogarty et al.
4,616,652 A  10/1986  Simpson
(Continued)

FOREIGN PATENT DOCUMENTS

CN   102510763 A   6/2012
DE     3819372 C1  1/1990
(Continued)

*Primary Examiner* — Bhisma Mehta
*Assistant Examiner* — William Frehe
(74) *Attorney, Agent, or Firm* — Seager, Tufte & Wickhem LLP (57) ABSTRACT

Guide extension catheters and methods of manufacturing and using guide extension catheters are disclosed. An example guide extension catheter may include a distal sheath having a proximal opening, a distal opening, and a central lumen extending therebetween. The guide extension catheter may also include a proximal shaft having an outer diameter smaller than an outer diameter of the distal sheath, the proximal shaft including a distal opening. The guide extension catheter may also include a coupling member for securing the distal sheath to the proximal shaft. The coupling member may include a distal portion attached to the distal sheath and a proximal portion disposed within the distal opening of the proximal shaft.

9 Claims, 6 Drawing Sheets

(51) Int. Cl.
*A61M 25/01* (2006.01)
*A61M 39/10* (2006.01)
*A61M 25/04* (2006.01)
*A61M 25/09* (2006.01)

(52) U.S. Cl.
CPC .... *A61M 25/0009* (2013.01); *A61M 25/0105* (2013.01); *A61M 25/0113* (2013.01); *A61M 25/0147* (2013.01); *A61M 25/04* (2013.01); *A61M 25/0905* (2013.01); *A61M 39/10* (2013.01); *A61M 25/0052* (2013.01); *A61M 2025/09058* (2013.01); *A61M 2025/09108* (2013.01); *Y10T 29/49826* (2015.01)

(58) Field of Classification Search
CPC .............. A61M 39/10; A61M 25/0023; A61M 25/0026; A61M 25/0028; A61M 25/0029; A61M 25/003; A61M 2025/0006; A61M 2025/0034
USPC .................. 604/103, 206, 240, 533, 538
See application file for complete search history.

(56) References Cited

U.S. PATENT DOCUMENTS

| | | |
|---|---|---|
| 4,762,129 A | 8/1988 | Bonzel |
| 5,120,323 A | 6/1992 | Shockey et al. |
| 5,232,445 A | 8/1993 | Bonzel |
| 5,267,982 A | 12/1993 | Sylvanowicz |
| 5,385,562 A | 1/1995 | Adams et al. |
| 5,441,489 A | 8/1995 | Utsumi et al. |
| 5,527,292 A | 6/1996 | Adams et al. |
| 6,066,126 A | 5/2000 | Li et al. |
| 6,575,958 B1 | 6/2003 | Happ et al. |
| 6,638,268 B2 | 10/2003 | Niazi |
| 6,695,793 B2 | 2/2004 | Brennan et al. |
| 6,953,454 B2 | 10/2005 | Peterson et al. |
| 7,232,452 B2 | 6/2007 | Adams et al. |
| 7,241,273 B2 | 7/2007 | Maguire et al. |
| 7,294,124 B2 | 11/2007 | Eidenschink |
| 7,316,678 B2 | 1/2008 | Nash et al. |
| 7,717,899 B2 | 5/2010 | Bowe et al. |
| 7,762,984 B2 | 7/2010 | Kumoyama et al. |
| 7,892,215 B2 * | 2/2011 | Melsheimer .............. A61F 2/95 604/103.04 |
| 8,048,032 B2 | 11/2011 | Root et al. |
| 8,142,413 B2 | 3/2012 | Root et al. |
| 8,292,850 B2 | 10/2012 | Root et al. |
| 2004/0059179 A1 * | 3/2004 | Maguire ................ A61M 25/10 600/16 |
| 2004/0116832 A1 | 6/2004 | Friedrich et al. |
| 2005/0148866 A1 | 7/2005 | Gunderson |
| 2006/0282041 A1 | 12/2006 | Melsheimer et al. |
| 2009/0177120 A1 | 7/2009 | Tockman et al. |
| 2010/0234876 A1 * | 9/2010 | Watson .................. A61B 18/02 606/194 |
| 2010/0318068 A1 * | 12/2010 | Melsheimer ...... A61M 25/0905 604/528 |
| 2013/0237962 A1 | 9/2013 | Kawai |

FOREIGN PATENT DOCUMENTS

| | | |
|---|---|---|
| EP | 0277366 A1 | 8/1988 |
| EP | 1639951 B1 | 4/2009 |
| WO | 03049798 A2 | 6/2003 |
| WO | 2011085180 A2 | 7/2011 |

* cited by examiner

GUIDE EXTENSION CATHETERS AND METHODS FOR MANUFACTURING THE SAME

CROSS-REFERENCE TO RELATED APPLICATIONS

This application claims priority under 35 U.S.C. § 119 to U.S. Provisional Application Ser. No. 61/678,502, filed Aug. 1, 2012, the entirety of which is incorporated herein by reference.

TECHNICAL FIELD

The present disclosure pertains to medical devices, and methods for manufacturing and using medical devices. More particularly, the present disclosure pertains to methods for manufacturing and using guide extension catheters.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a guide extension catheter. An example guide extension catheter may include a distal sheath having a proximal opening, a distal opening, and a central lumen extending therebetween. The guide extension catheter may also include a proximal shaft having an outer diameter smaller than an outer diameter of the distal sheath, the proximal shaft including a distal opening. The guide extension catheter may also include a coupling member for securing the distal sheath to the proximal shaft. The coupling member may include a distal portion attached to the distal sheath and a proximal portion disposed within the distal opening of the proximal shaft.

A method for manufacturing a guide extension catheter is also disclosed. The method may include providing a distal sheath having an outer diameter and a central lumen, providing a proximal shaft having a distal opening and an outer diameter smaller than the outer diameter of the distal sheath, providing a coupling member having a proximal portion and a distal portion, securing the distal portion of the coupling member to the distal sheath, and inserting the proximal portion of the coupling member into the distal opening of the proximal shaft.

A method for accessing a coronary artery is also disclosed. The method may include providing a guide catheter and advancing the guide catheter through a blood vessel to a position adjacent to an ostium of a coronary artery. The method may also include providing a guide extension catheter. The guide extension catheter may include a distal sheath having a proximal opening, a distal opening, and a central lumen extending therebetween, a proximal shaft having an outer diameter smaller than an outer diameter of the distal sheath, the proximal shaft including a distal opening, and a coupling member for securing the distal sheath to the proximal shaft. The coupling member may include a distal portion attached to the distal sheath and a proximal portion disposed within the distal opening of the proximal shaft. The method may also include advancing the guide extension catheter through the guide catheter to a position where at least a portion of the distal sheath member extends distally beyond a distal end of the guide catheter and into the coronary artery and advancing a treatment catheter through the guide catheter.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

For purposes of this disclosure, "proximal" refers to the end closer to the device operator during use, and "distal" refers to the end further from the device operator during use.

Minimally-invasive cardiac interventions such as percutaneous transluminal coronary angioplasty are widely utilized throughout the world. These procedures may include the use of a guide catheter. For example, a guide catheter may be advanced through a blood vessel such as the aorta to a position adjacent to the ostium of a (e.g., left and/or right) coronary artery. When so positioned, a treatment catheter (e.g., balloon catheter, stent delivery system, etc.) may be advanced through the guide catheter and into the coronary artery to a target location where the treatment catheter may be used to perform the appropriate cardiac intervention.

In order for the treatment catheter to efficiently reach the intended target location, maintaining the position of the guide catheter at the ostium of the coronary artery may be desirable. For example, given that the heart may be beating during the intervention (and/or other factors), the guide catheter may lose its positioning or otherwise be shifted so that it no longer is positioned to efficiently guide the treatment catheter to the coronary arteries. This may include a distal end of guide catheter being shifted away from the ostium of the coronary artery. Because of the shift away from the ostium, access to the coronary arteries may require repositioning of the guide catheter in order to bring the distal end back into engagement with the ostium of the coronary artery.

Disclosed herein are medical devices and methods for making and using medical devices that may improve access to the coronary arteries. For example, disclosed herein are guide extension catheters that are generally configured to extend through a guide catheter to a position where the distal end of the guide extension catheter extends beyond the distal end of the guide catheter into the coronary artery. Because, for example, the guide extension catheter may extend beyond the distal end of the guide catheter, the guide extension catheter may extend beyond the ostium of the coronary artery and into a portion of the coronary artery. By extending beyond the ostium, the guide extension catheter may stabilize the positioning of the guide catheter and allow for improved access to the coronary artery for a number of cardiac interventions.

Figure 1:
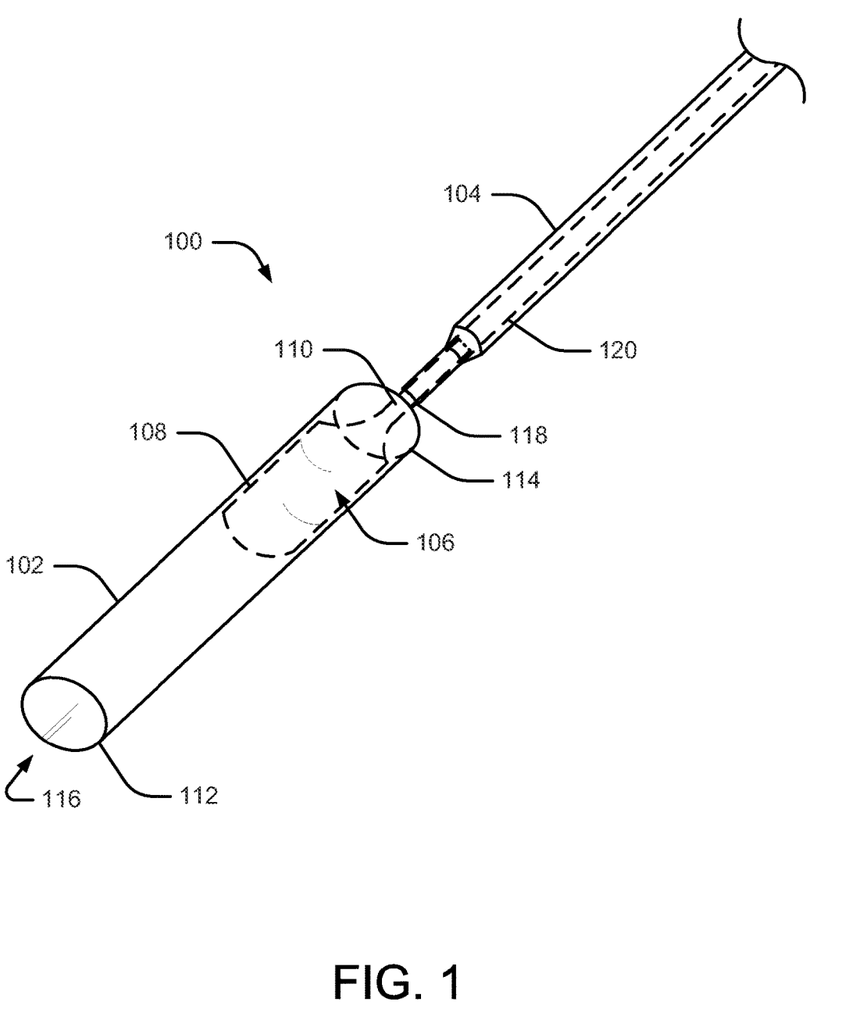
FIG. 1 depicts an exemplary guide extension catheter.

FIG. 1 depicts an exemplary guide extension catheter 100. The guide extension catheter 100 may generally be adapted to be slidably disposed within a guide catheter (not shown). The guide extension catheter 100 may include a distal sheath 102 attached to a proximal shaft 104 through a coupling member 106. The coupling member may include a distal portion 108 and a proximal portion 110. The distal portion 108 may attach to the distal sheath 102 and the proximal portion 110 may attach to the proximal shaft 104.

The distal sheath 102 may be a sheath or tubular member having a distal end 112, a proximal end 114, and a lumen 116 passing between them. The distal sheath 102 may be adapted to coaxially slide into the lumen of a desired guide catheter. The distal sheath 102 may assume a suitable cross-sectional shape such as circular, oval, polygonal or the like. In some embodiments, the cross-sectional shape of the distal sheath 102 may be similar to the cross-sectional shape of the desired guide catheter's lumen. The distal sheath 102 may assume maximum cross-sectional dimensions that may allow the distal sheath 102 to coaxially slide into the desired guide catheter. In some other embodiments, however, the cross-sectional dimensions of the distal sheath 102 may be less than the allowable maximum. For example, in an 8 F guide catheter, the distal sheath 102 may assume a 7 F, 6 F, 5 F, or lesser diameter, where 'F', also known as French catheter scale, is a unit to measure catheter diameter (1 F=⅓ mm). In general, the lumen 116, and hence the distal sheath 102, may be large enough to pass one or more medical devices, such as a treatment catheter (e.g., balloon catheter, stent delivery system, or the like) and a guidewire therethrough.

The length of the distal sheath 102, in general, may be substantially less than the length of the guide catheter; however, the distal sheath 102 may be designed with any desired length according to a desired application. The distal end 112 may be atraumatic to prevent inadvertent injury to the vascular tissue upon distal extension of the distal sheath 102 out of the guide catheter. Additionally, the distal sheath 102 or a portion of it may be selectively steerable. Mechanisms such as pull wires, control wires, motors, hydraulics, or other actuators may be used to selectively steer the distal sheath 102.

Distal sheath 102 may include one or more polymers including any of those disclosed herein. This may include the use of polymers with a differing durometer along the length the distal sheath 102. For example, a more proximal section of the distal sheath 102 may include a polymer with a higher durometer and a more distal section of the distal sheath 102 may include a polymer with a lower durometer. Portions of all of the length of the distal sheath 102 may be loaded with or otherwise include a radiopaque material. Distal sheath 102 may also include a reinforcement member. The form of the reinforcement member may vary. For example, the reinforcement member may include a braid, coil, mesh, or the like.

The proximal shaft 104 may be an elongate shaft, ribbon, or tube attached to the coupling member 106. In at least some embodiments, proximal shaft 104 may have a distal opening 118 in communication with a lumen 120 extending through at least a portion of the proximal shaft 104. The proximal shaft 104 may be of any cross-sectional shape, such as, square, circular, oval, polygonal, or irregular. The cross-sectional dimensions of the proximal shaft 104 may be substantially smaller than the cross-sectional dimensions of the distal sheath 102. In general, the cross-sectional dimensions of the proximal shaft 104 may be small enough to not to obstruct other medical devices extending through the guide catheter (and the distal sheath 102). The proximal shaft 104 may be long enough to allow an operator to extend a desired length of the guide extension catheter 100 distally out the guide catheter by distally urging the proximal shaft 104 distally. Generally, the proximal shaft 104 may be long enough to make the guide extension catheter 100 longer than the guide catheter.

Coupling member 106 may be understood to be an intermediate member designed to join the distal sheath 102 to the proximal shaft 104. In addition, coupling member may provide a low profile attachment mechanism that forms a generally smooth transition with the proximal shaft 104 and provides desirable pushability and torque transmission along the guide extension catheter 100. The distal portion 108 of proximal shaft 104 may be adapted to be disposed within lumen 116 and to attach to the inner wall of distal sheath 102. Alternatively, the distal portion 108 may be attached to the outer wall of distal sheath 102, be embedded within distal sheath 102, or otherwise secured to distal sheath 102 in other suitable manners.

The distal portion 108 of coupling member 106 may have cross-sectional shape and dimensions adapted to axially align and fit into the lumen 116. In some embodiments, the distal portion 108 may have an arched, semi-annular, or annular shape designed with a maximum possible radius that may allow the distal portion 108 to fit within the lumen 116. In general, the distal portion 108 may assume a shape substantially similar to the shape of the distal sheath 102 and may be large enough to allow easy passage of medical devices through lumen 116. The length of the distal portion 108 may be designed to provide optimal attachment between the distal sheath 102 and coupling member 106, and the length may depend upon method of attachment and the required strength of the attachment.

The proximal portion 110 of coupling member 106 may be an elongate portion extending proximally from the distal portion 108. The proximal portion 110 may assume any profile that may allow it to attach with the proximal shaft 104. For example, the proximal portion 110 may have a circular, oval, polygonal, flat, or irregular profile. In some embodiments, the proximal portion 110 may have a flat ribbon-like profile. Such shapes may allow the proximal portion 110 to be inserted within the distal opening 118 of proximal shaft 104 so that coupling member 106 may be secured to proximal shaft (e.g., via stamping, crimping, welding, gluing, or otherwise attached with other suitable methods). Alternatively, proximal portion 110 may be secured to an outer surface of proximal shaft 104 using a suitable attachment technique.

A wide range of materials may be used to make the distal sheath 102, proximal shaft 104, and coupling member 106, such materials may include metals, polymers, metal-polymer composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenyleneterephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These are just examples and not provided by way of limitation.

Guide extension catheter 100 may also include a number of coatings that may, for example, reduce friction. For example, proximal shaft 104 and/or distal sheath 102 may have an inner and/or outer coating that includes a hydrophilic polymer that may reduce friction during tracking. An example coating may include BAYER CL-100, BIOSLIDE, NG-HPC, SLIP COAT, MDX, or the like. These are just examples. Other materials are contemplated including those disclosed herein.

The coupling member 106 may attach to the distal sheath 102 and the proximal shaft 104 through a variety of different mechanisms. Suitable mechanisms may include adhesives, welding, stamping, soldering, riveting, or bolting. For example, in some embodiments, the distal portion 108 may be attached to the distal sheath 102 by use of polymer reflow, thermal bonding, adhesives, soldering, or welding. The proximal portion 110 may be riveted, bolted, crimped, stamped, or welded to the distal opening 118 of the proximal shaft 104.

Those in the art may choose from among a wide range of methods available for manufacturing the guide extension catheter 100. Some such exemplary methods are discussed in the following sections. The following sections focus on methods for making different embodiments of the coupling member 106 and methods for attaching these embodiments to the distal sheath 102 and the proximal shaft 104.

Figure 5A:
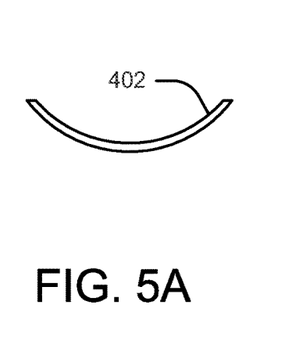
Figures 5B, 5C:
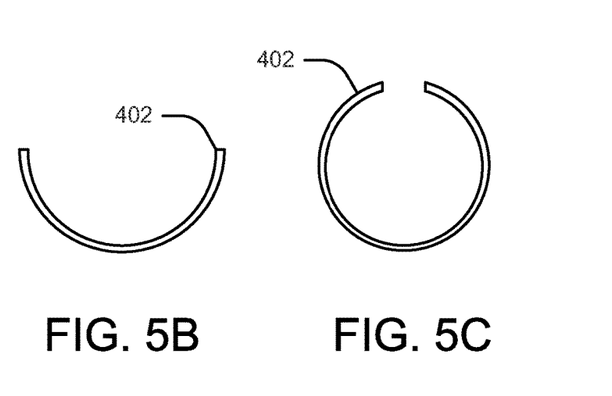
Figures 6A, 6B:
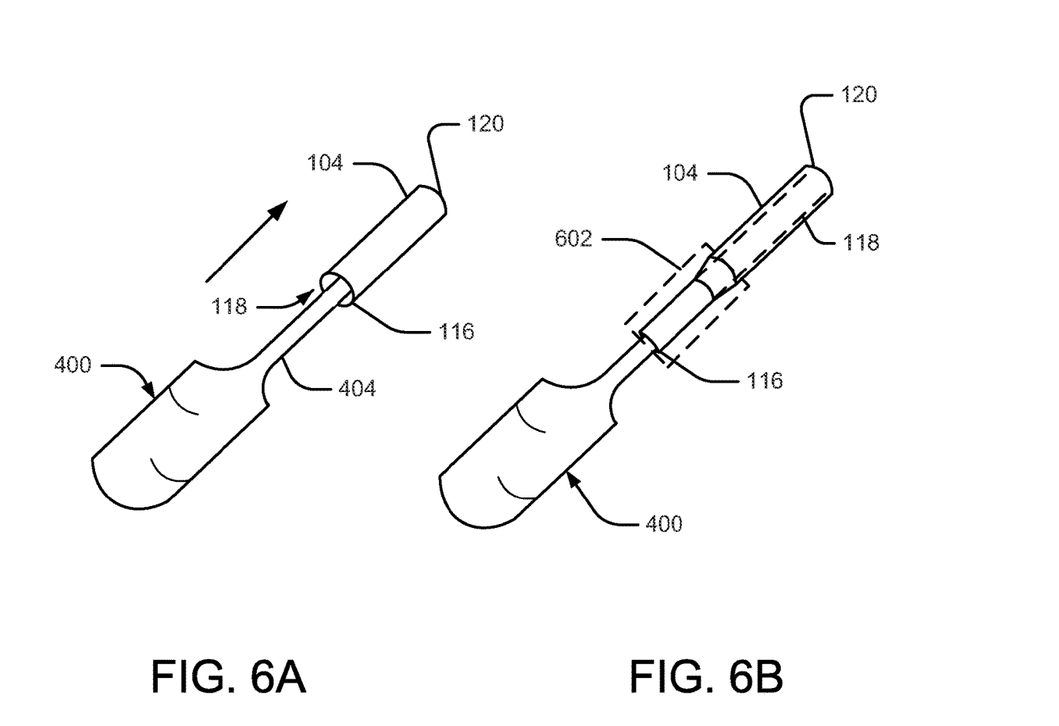
Figure 7:
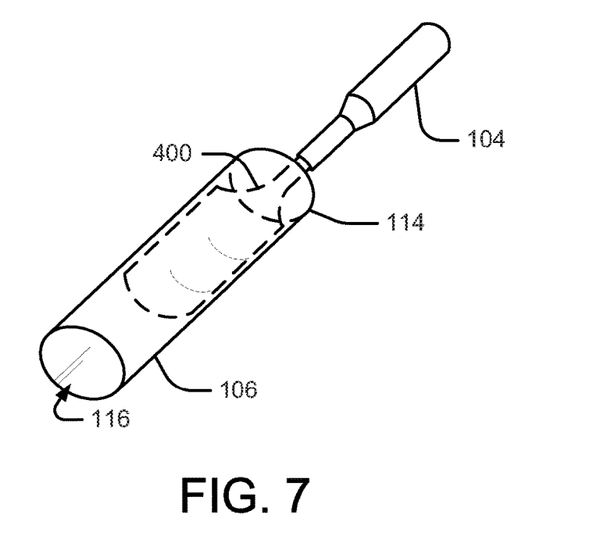

FIGS. 2-7 illustrate an exemplary method of manufacturing guide extension catheters including those disclosed herein. The disclosure includes methods for forming an exemplary embodiment of the coupling member 400 from sheet metal (shown in FIGS. 2-5C), attaching the coupling member 400 to proximal shaft 104 (FIGS. 6A-6B), and attaching the coupling member 400 to a distal sheath 102 (FIG. 7).

Figure 2:
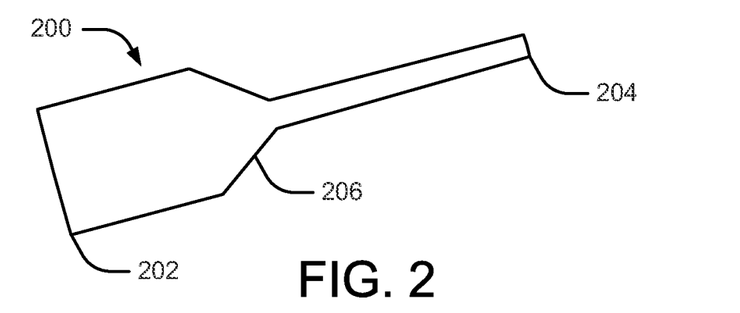
FIGS. 2-7 illustrate an exemplary method of manufacturing the guide extension catheter.

Initially, as shown in FIG. 2, a metal sheet 200, made of a suitable material (including those materials disclosed herein) such as a metal, may be cut into a suitable shape. For example, as shown, a suitably shaped sheet 200 may have a wide distal portion 202, a narrow proximal portion 204, and a tapering mid portion 206 occupying a small region between the distal and proximal portions 202/204.

Figure 3:
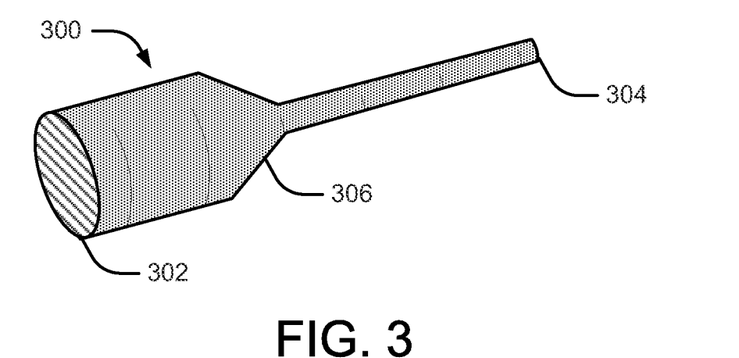
Figure 4:
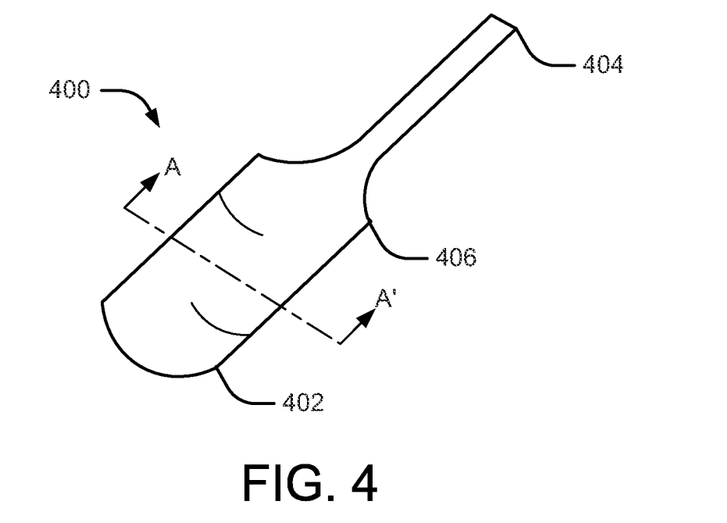

The sheet 200 (FIG. 2) may be stamped or press rolled over a tapered mandrel 300, shown in FIG. 3, to form a desired shape of the coupling member 400 (FIG. 4). The mandrel 300 may have distal portion 302 with a larger diameter than the proximal portion 304. A tapered mid portion 306 may join the distal and proximal portions 302, 304. The cross-sectional dimensions of the mandrel 300 may be designed to form the sheet 200 into the desired coupling member 400. As shown in FIG. 4, after stamping or press rolling, the distal portion 202, and the tapered portion 206 may assume a curved profile forming the distal portion 402 of the coupling member 400, and proximal portion 204 may remain in a flat profile forming proximal portion 404 of the coupling member 400. A tapered mid portion 406 is disposed between the distal portion 302 and the proximal portion 304. The profile of the distal portion 402 may vary in different embodiments.

FIGS. 5A-5C are cross-sectional views of three different embodiments of the coupling member 400 taken across the plane A-A", shown in FIG. 4. In an embodiment, shown in FIG. 5A, the distal portion 402 may have an arched profile, extending across substantially less than 180° of arc. In another embodiment, shown in FIG. 5B, the distal portion 402 may have a semi-circular profile. Similarly, in another embodiment, shown in FIG. 5C, the distal portion 402 may have a nearly circular profile. In general, the distal portion 402 may have any profile according to the desired embodiments.

As shown in FIGS. 6A-6B, the coupling member 400 may attach to the proximal shaft 104. The proximal portion 404 may be inserted into the distal opening 118 of proximal shaft 104 and proximal shaft 104 may be stamped or crimped. That operation forms a joint 602, thereby attaching the coupling member 400 to proximal shaft 104. For this purpose, the proximal portion 404 may be cut, shaped, or bent to fit into the distal opening 118, if desired.

The coupling member 400 may attach to the distal sheath 102, as illustrated in FIG. 7. This may include the use of an adhesive. Alternatively, the coupling member 400 may be disposed along the outer surface of the distal sheath 102 (or the inner surface of the distal sheath 102) and attached to the distal sheath 102 with a polymer reflow process. The polymer reflow process may include disposing one or more additional layers of polymer material over the coupling member 400 and the application of heat to bond the coupling member 400 to the distal sheath 102.

The attachment of coupling member 400 to the distal sheath 102 may be enhanced by forming one or more openings, holes, grooves, or the like in the coupling member 400. This may allow polymeric material to flow into or along the openings, holes, grooves, or the like so that coupling member 400 may mechanically interlock with distal sheath 102 or otherwise improve the tensile strength of the bond between coupling member 400 and distal sheath 102.

Figures 8, 9:
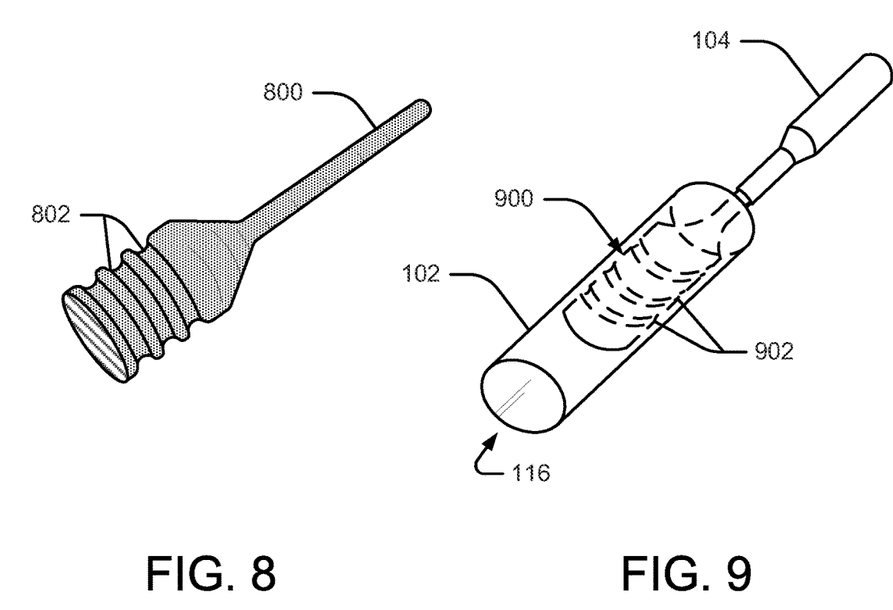
FIGS. 8-9 exhibit an exemplary alternative method of attaching the coupling member to the distal sheath.

FIGS. 8-9 exhibit another exemplary method of attaching an embodiment of the coupling member 900, similar to coupling member 400, to the distal sheath 102. In this method, the sheet 200, shown in FIG. 2, is press rolled or stamped over a tapered mandrel 800 (Shown in FIG. 8), similar to mandrel 300, having one or more grooves 802 on its surface. Upon stamping or press rolling the sheet 200, the coupling member 900 may be produced having grooves 902 corresponding to the grooves 802 in mandrel 300. Any of the coupling members disclosed herein may utilize grooves 902 or other similar grooves, holes, openings, or the like. The grooves 902 may extend along the full width of the coupling member 900. Alternatively, side portions of the coupling member 900 may include grooves 902 and/or side portions of the grooves 902 may be removed to define cutouts. The grooves 902 either vary in form and, in some embodiments, may be linear, as shown, or they may follow one or more patterns such as sinusoidal, cosine or the like. Employing such patterns may improve strength of the bond between the coupling member 900 and the distal sheath 102.

FIGS. 10A-10D illustrate another exemplary method of making an embodiment of the disclosed guide extension catheter. The method includes forming a coupling member 1004 (FIG. 10B) by cutting a hypotube 1000 (FIG. 10A), removing material from a portion of the length of the hypotube 1000, leaving a proximal ribbon portion 1008, and attaching the coupling member 1004 to the proximal shaft 104 and distal sheath 102.

Figure 10A:
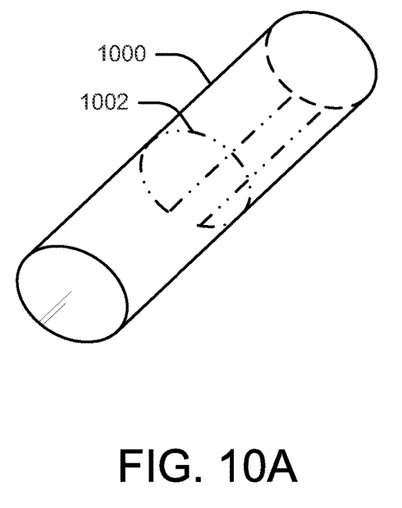
FIGS. 10A-10D illustrate another exemplary method of manufacturing the guide extension catheter.
Figure 10B:
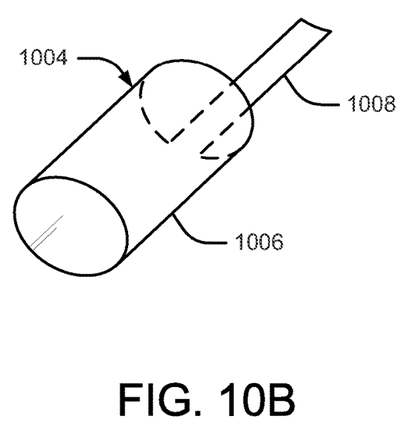

The hypotube 1000, shown in FIG. 10A, may be cut along the line 1002 to form the coupling member 1004, shown in FIG. 10B, using any cutting mechanism, such as, a laser, waterjet, or a mechanical cutting tool. The line 1002 provides for a merely exemplary shape of the coupling member 1004, and the hypotube 1000 may be cut into many other shapes to form the coupling member 1004. When the hypotube 1000 is cut into the desired shape, the resultant coupling member 1004 may have a distal portion 1006 and a proximal ribbon portion 1008. The distal portion 1006, similar to distal portion 402 shown in FIGS. 5A-C, may have a circular, semi-circular, or arched profile, and the proximal ribbon portion 1008 may have a ribbon like profile.

Figure 10C:
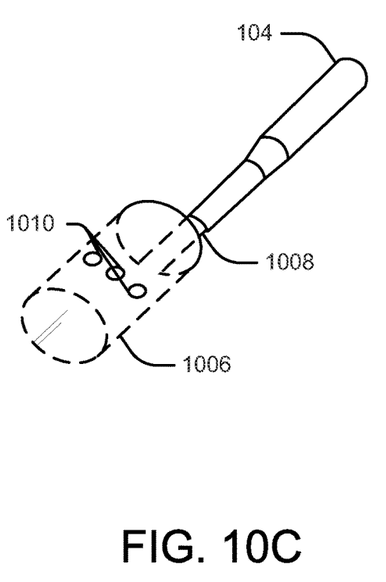

As shown in FIG. 10C, similar to the method of FIGS. 2-7, the proximal ribbon portion 1008 may be attached to the proximal shaft 104 by inserting the proximal ribbon portion 1008 into the distal opening 118 of proximal shaft 104 and crimping or stamping proximal shaft 104. However, in some other embodiments, methods such as gluing, welding, riveting, bolting, or the like may be used to attach the proximal ribbon portion 1008 to the proximal shaft 104.

Figure 10D:
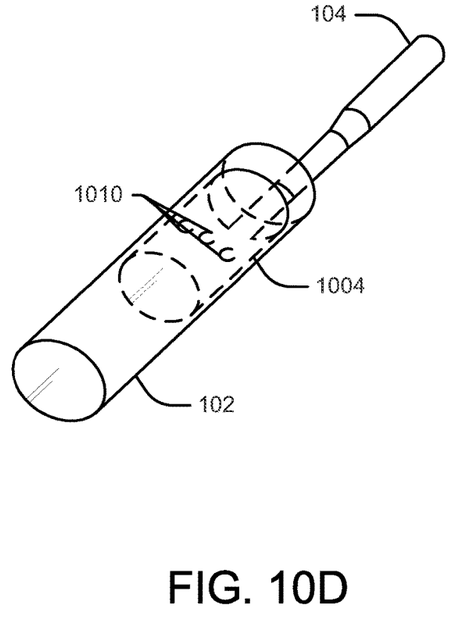

Further, one or more holes 1010 may be formed into the distal portion 1006. Referring to FIG. 10D, the holes 1010, similar to grooves 902, shown in FIG. 9, may be filled with polymer reflow material and then employed in joining the distal portion 1006 with the distal sheath 102. This may improve the integrity of the bond between coupling member 1004 and distal sheath 102. Any of the coupling members disclosed herein may utilize holes 1010 or other similar holes, grooves, openings, or the like.

Figure 11:
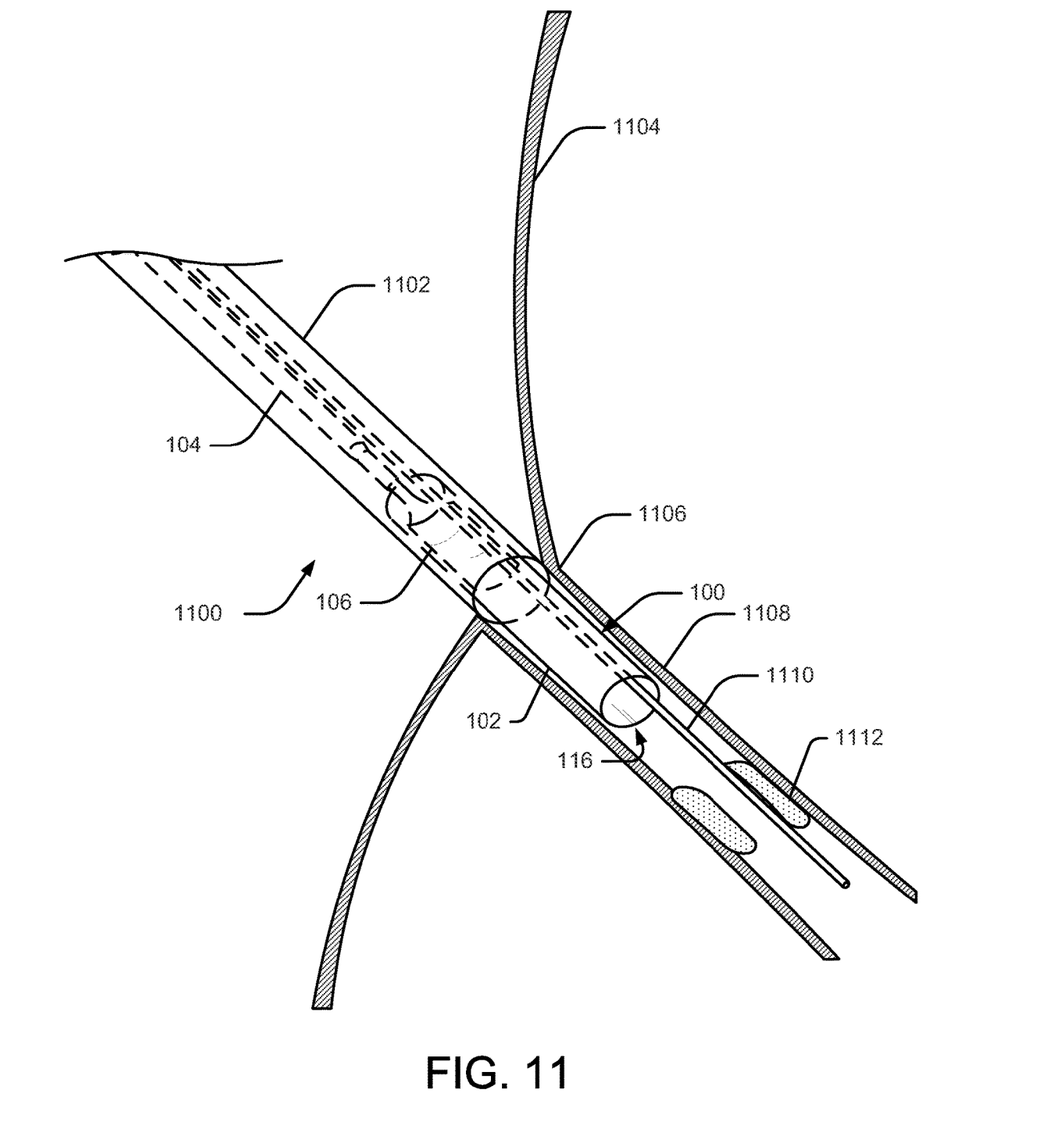
FIG. 11 depicts an exemplary method of using the guide extension catheter.

FIG. 11 depicts an exemplary method of using the guide extension catheter 100. More specifically, FIG. 11 shows the use of guide extension catheter 100 in interventional cardiology. The guide extension catheter 100 may be used within a catheter assembly 1100 including a guide catheter 1102, the guide extension catheter 100 and other medical devices, such as balloon catheter, guidewire, etc. The method may include advancing the guide catheter 1102 within a blood vessel 1104 (e.g., the aorta) to the ostium 1106 of an adjoining coronary artery 1108. The guide extension catheter 100 may then be advanced within the guide catheter 1102 such that the guide extension catheter 100 extends beyond the distal end of the guide catheter 1102. Further, the method may include advancing other medical devices such as a guidewire 1110 through the distal sheath 102 and performing the desired interventional cardiology procedure such as, stenting, or ballooning of blood vessels.

Further, if the coronary artery 1108 has any lesions, such as constrictions 1112, the guidewire 1110 may contact the constrictions 1112 and apply a force on the guide catheter 1102. In the absence of guide extension catheter 100, such contact may dislodge the guide catheter 1102 from the ostium 1106, which may cause problems to the operator as well as inadvertent damage to the surrounding tissue. In the presence of the guide extension catheter 100, however, the guide catheter 1102 may not dislodge from its position, thereby allowing the operator to work efficiently and preventing any inadvertent injury to nearby tissue.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A guide extension catheter, comprising:
   a distal sheath having a proximal opening, a distal opening, and a central lumen extending therebetween;
   a proximal shaft having an outer diameter smaller than an outer diameter of the distal sheath, the proximal shaft including a distal opening; and
   a coupling member extending between the distal sheath and the proximal shaft, the coupling member including a distal portion fixedly attached to the distal sheath and a non-tubular proximal portion fixedly attached within the distal opening of the proximal shaft.

2. The guide extension catheter of claim 1, wherein the coupling member further includes one or more grooves on the distal portion.

3. The guide extension catheter of claim 1, wherein the coupling member has one or more holes formed therein.

4. The guide extension catheter of claim 3, wherein the one or more holes are formed on the distal portion of the coupling member and facilitate fixedly attaching the coupling member to the distal sheath.

5. The guide extension catheter of claim 1, wherein the distal sheath includes a reinforcing member.

6. The guide extension catheter of claim 1, wherein the proximal shaft includes a metallic hypotube.

7. The guide extension catheter of claim 1, wherein the proximal shaft includes a polymer.

8. The guide extension catheter of claim 1, wherein the non-tubular proximal portion of the coupling member is fixedly attached to the proximal shaft with a crimp bond.

9. The guide extension catheter of claim 1, wherein the non-tubular proximal portion of the coupling member is fixedly attached to the proximal shaft with a stamped bond.

\* \* \* \* \*